(12) United States Patent
Beijert

(10) Patent No.: US 9,234,853 B2
(45) Date of Patent: Jan. 12, 2016

(54) PROBE APPARATUS

(71) Applicant: BEIJERT ENGINEERING, Al Zwaag (NL)

(72) Inventor: Oscar Beijert, Elspeet (NL)

(73) Assignee: BEIJERT ENGINEERING, Al Zwaag (NL)

( * ) Notice: Subject to any disclaimer, the term of this patent is extended or adjusted under 35 U.S.C. 154(b) by 397 days.

(21) Appl. No.: 13/912,359

(22) Filed: Jun. 7, 2013

(65) Prior Publication Data

US 2014/0015955 A1 Jan. 16, 2014

Related U.S. Application Data

(60) Provisional application No. 61/657,558, filed on Jun. 8, 2012.

(51) Int. Cl.
*G01R 31/20* (2006.01)
*G01N 21/95* (2006.01)
*G01R 31/28* (2006.01)

(52) U.S. Cl.
CPC ............ *G01N 21/95* (2013.01); *G01R 31/2801* (2013.01); *G01R 31/2806* (2013.01)

(58) Field of Classification Search
CPC .................................................... G01N 21/95
See application file for complete search history.

(56) References Cited

U.S. PATENT DOCUMENTS

| 3,626,460 | A | * | 12/1971 | Miller | B41B 17/02 396/554 |
|---|---|---|---|---|---|
| 4,155,173 | A | * | 5/1979 | Sprandel | G01B 5/008 33/1 M |
| 5,104,621 | A | * | 4/1992 | Pfost | G01N 21/253 422/521 |
| 6,058,618 | A | * | 5/2000 | Hemmelgarn | G01B 5/008 33/503 |
| 6,404,212 | B1 | * | 6/2002 | Mehta | G01R 31/2887 324/750.22 |
| 7,449,905 | B2 | * | 11/2008 | Shi | G01R 31/2642 324/750.03 |
| 2007/0126441 | A1 | | 6/2007 | Mochizuki et al. | |
| 2007/0200581 | A1 | * | 8/2007 | Shi | G01R 31/2642 324/750.08 |
| 2007/0257686 | A1 | * | 11/2007 | Beijert | G01R 31/2886 324/750.01 |
| 2011/0089965 | A1 | * | 4/2011 | Endres | G01R 35/00 324/755.01 |
| 2012/0126843 | A1 | | 5/2012 | Shibahara | |

FOREIGN PATENT DOCUMENTS

KR 2009-0068902 A 6/2009

OTHER PUBLICATIONS

International search report and written opinion for PCT/IB2013/001201 dated Oct. 17, 2013.

* cited by examiner

*Primary Examiner* — Jermele M Hollington
(74) *Attorney, Agent, or Firm* — Patterson & Sheridan, LLP

(57) ABSTRACT

The present invention generally relates to methods and apparatuses for ensuring the integrity of probe card assemblies, verifying that probe cards are ready for testing, and allowing analysis of probe card performance characteristics. In one embodiment, an apparatus allows rework of a probe card at an angle from a front position of the apparatus.

21 Claims, 17 Drawing Sheets

PROBE APPARATUS

CROSS-REFERENCE TO RELATED APPLICATIONS

This application claims benefit of U.S. Provisional Patent Application Ser. No. 61/657,558 (BEIJ/0004USL), filed Jun. 8, 2012, which is herein incorporated by reference.

BACKGROUND OF THE INVENTION

1. Field of the Invention

Embodiments of the present invention generally relate to integrated circuit testing, and more particularly, to apparatuses and methods for testing probe cards used to test integrated circuits on a wafer.

2. Description of the Related Art

Probe card test and verification systems are commonly used as production tools for the characterization of probe cards (used in testing integrated circuit devices/substrates) before and after use and to facilitate rework of probe cards that do not conform to predefined standards. Such systems typically consist of a computer, a precision measurement system, a software based vision system, and precision motion control and measurement system. Such equipped systems allow for the measurement and adjustment of probe card planarization, visual X/Y location and adjustment, probe contact resistance, leakage and component measurements.

Electrical parameters including contact resistance and leakage may also be measured against reference values and an indication may be provided as to whether a probe card assembly under test has passed or failed. If a failure is determined, a full report may be printed to accompany the card for rework. Quick verification provided by such systems may validate that a probe card assembly is ready for test or is in need of rework.

Therefore, there is a continuing need to improve such systems to that ensure the integrity of probe card assemblies, verify that probe cards are ready for testing, and allow analysis of probe card performance characteristics.

SUMMARY OF THE INVENTION

The present invention generally relates to methods and apparatuses for ensuring the integrity of probe card assemblies, verifying that probe cards are ready for testing, and allowing analysis of probe card performance characteristics. In one embodiment, an apparatus allows rework of a probe card at an angle from a front position of the apparatus.

In one embodiment, a probe card analyzer apparatus is disclosed. The apparatus comprises a table body; a first support arm extending away from a first corner of the table body; a second support arm extending away from a second corner of the table body, the second support arm extending substantially parallel to the first support arm; a first track coupled to the first support arm; a second track coupled to the second support arm; a first sample table arm coupled to the first track and movable along the first track; a second sample table arm coupled to the second track and movable along the second track, the second sample table arm substantially parallel to the first sample table arm; a sample table rotatably coupled to the first sample table arm and the second sample table arm such that the sample table is rotatable about an axis.

In another embodiment, a method for moving a platform is disclosed. The method comprises moving a first sample table arm along a first track that is coupled to a first support arm that is coupled to a first corner of a table body; moving a second sample table arm along a second track that is coupled to a second support arm that is coupled to a second corner of the table body, wherein the second support arm is in a plan substantially parallel to plane in which the first support arm is disposed; and rotating a sample table about an axis, wherein the sample table is rotatably coupled to the first sample arm and the second sample arm.

In another embodiment, a probe card analyzer apparatus comprises a table body; a first support arm extending away from a first corner of the table body; a second support arm extending away from a second corner of the table body, the second support arm extending substantially parallel to the first support arm; a first track coupled to the first support arm; a second track coupled to the second support arm; a first sample table arm pivotably coupled to the first track and movable along the first track; a second sample table arm pivotably coupled to the second track and movable along the second track, the second sample table arm is substantially parallel to the first sample table arm; a third sample table arm pivotably coupled to the table body; a fourth sample table arm pivotably coupled to the table body; and a sample table rotatably coupled to the first sample table arm, the second sample table arm, the third sample table arm and the fourth sample table arm such that the sample table is rotatable about one or more axis.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION

The present invention generally relates to methods and apparatuses for ensuring the integrity of probe card assemblies, verifying that probe cards are ready for testing, and allowing analysis of probe card performance characteristics. In one embodiment, an apparatus allows rework of a probe card at an angle from a front position of the apparatus. Suitable apparatus, such as a Manager, that may be used to practice the embodiments described herein may be obtained from Stichting Continuities Beijert Engineering, The Netherlands. It is to be understood that the embodiments discussed herein may be practiced on other apparatus, including those sold by other manufacturers. The apparatus may be used to process probe cards that are 200 mm in diameter, 300 mm in diameter, 450 mm in diameter and any diameter probe cards desired.

Figure 1:
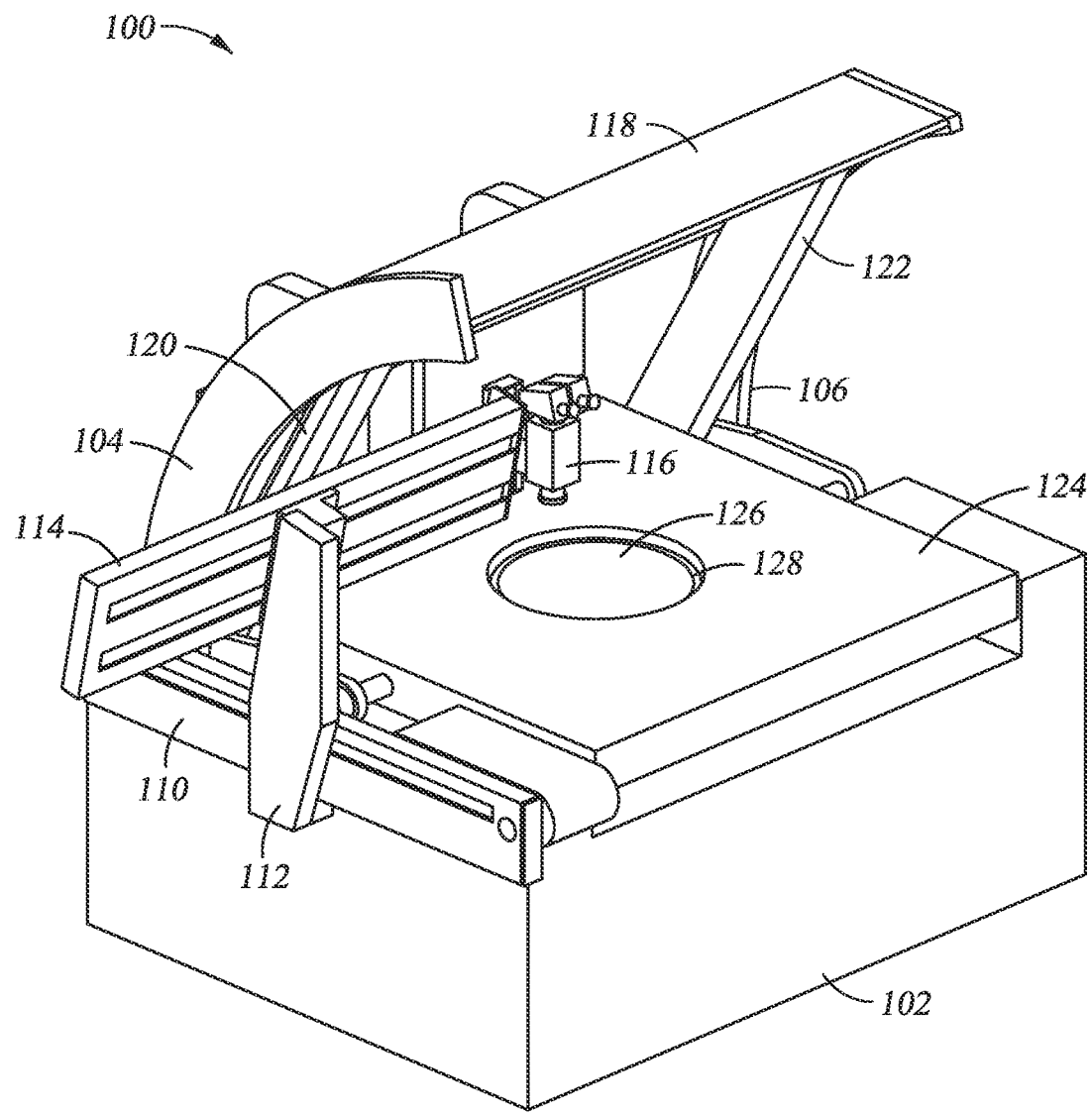
FIG. 1 is a schematic isometric illustration of a probe card analyzer apparatus according to one embodiment.

FIG. 1 is a schematic isometric illustration of a probe card analyzer apparatus 100 according to one embodiment. Apparatus 100 comprises a table body 102. A first support arm 104 extends away from a first corner of table body 102. A second support arm 106 extends away from a second corner of table body 102. Second support arm 106 extends substantially parallel to the first support arm 104. Apparatus 100 may comprise a first analysis arm 110 coupled to first support arm 104 and to be pivotable about an axis that is adjacent to a third corner of the table body 102. The first analysis arm 110 may pivot about the axis adjacent the third corner and along the first support arm 104.

Attached to the first analysis arm 110 is a second analysis arm 112 that extends substantially perpendicular to the first analysis arm 110. The second analysis arm 112 is movable along the first analysis arm 110 such that the first analysis arm 110 acts, in essence, as a track. Coupled to the second analysis arm 112 is an analysis table 114 that is movable perpendicular to the second analysis arm 112 in the direction that the second analysis arm 112 extends from the first analysis arm 110. Coupled to the analysis table 114 is a microscope 116 that is used to measure/analyze probe cards. As will be discussed below, the first analysis arm 110 pivots about an axis to cause an end of the first analysis arm 110 to move along the first support arm 104. Additionally, the second analysis arm 112 may slide along the first analysis arm 110 and the analysis table 114 may move in a plane perpendicular to the second analysis arm 112 to move the microscope 116 into and out of the desired inspection location.

To work on a probe card, the technician needs to be able to access both sides of the probe card so that the technician can access and rework the probes with tweezers to realign the pins.

As shown in FIG. 1, the first support arm 104 and the second support arm 106 are coupled together by a beam 118 that ensures the first support arm 104 and the second support arm 106 remain substantially stationary during operation of the apparatus 100. A first track 120 is coupled to the first support arm 104 and a second track 122 is coupled to the second support arm 106. The tracks 120, 122 are used to move the sample table 124 to multiple positions. The sample table 124 has an opening therethrough where a specimen cylinder 128 supports an alignment plate 126. A microscope 116 is present that includes a repair robot that can be used to rework and change a pin on a probe card. A laser is also present on the microscope structure so that a new probe can be welded onto the probe card. As will be discussed below, the microscope works with a camera that is positioned within the specimen cylinder 128 and a vision system to tell the technician that the probe pin is mounted correctly.

Figure 2:
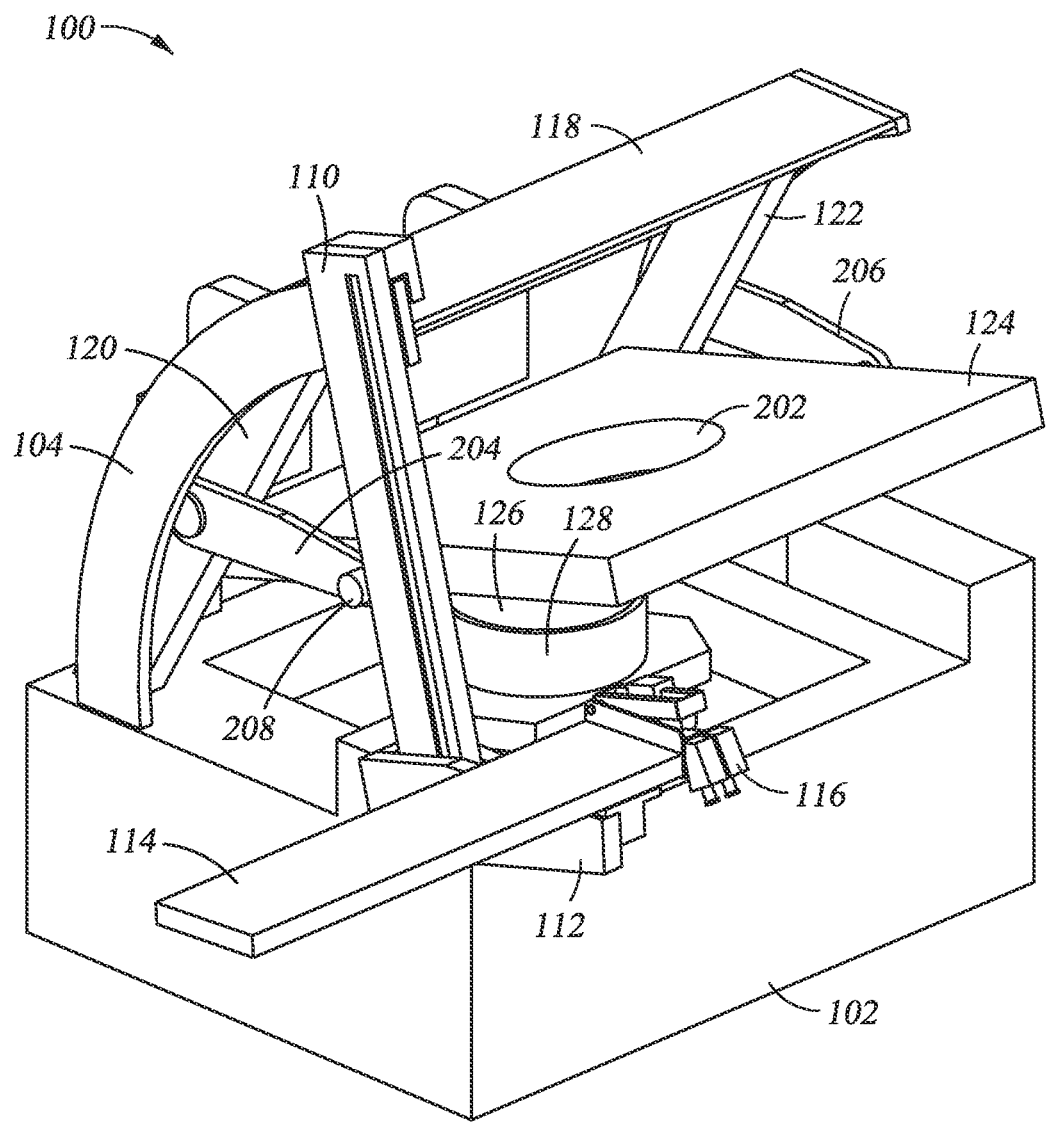
FIG. 2 is a schematic isometric illustration of the probe card analyzer apparatus of FIG. 1 with the analysis table and sample table in a second position.

FIG. 2 shows the sample table 124 and the analysis table 114 moved into a second position. The third arm 110 has slid along the first arm 104 while pivoting about an axis near the third corner of the body 102. By so moving the analysis table 114, the microscope 116 and analysis table 114 are sufficiently out of the way so that the sample table 124 may move.

As shown in FIG. 2, the sample table 124 is coupled to a first sample table arm 204 and a second sample table arm 206 and can rotate about an axis 208. The first sample table arm 204 slides along the first track 120 while the second sample table arm 206 slides along the second track 122 to move the sample table 124 away from the body 102. During the movement away from the body 102, the sample table 124 rotates about the axis 208 while the arms 204, 206 slide along the tracks 120, 122. In the new position, the opening 202 through the sample table 124 is more clearly visible.

Figure 3:
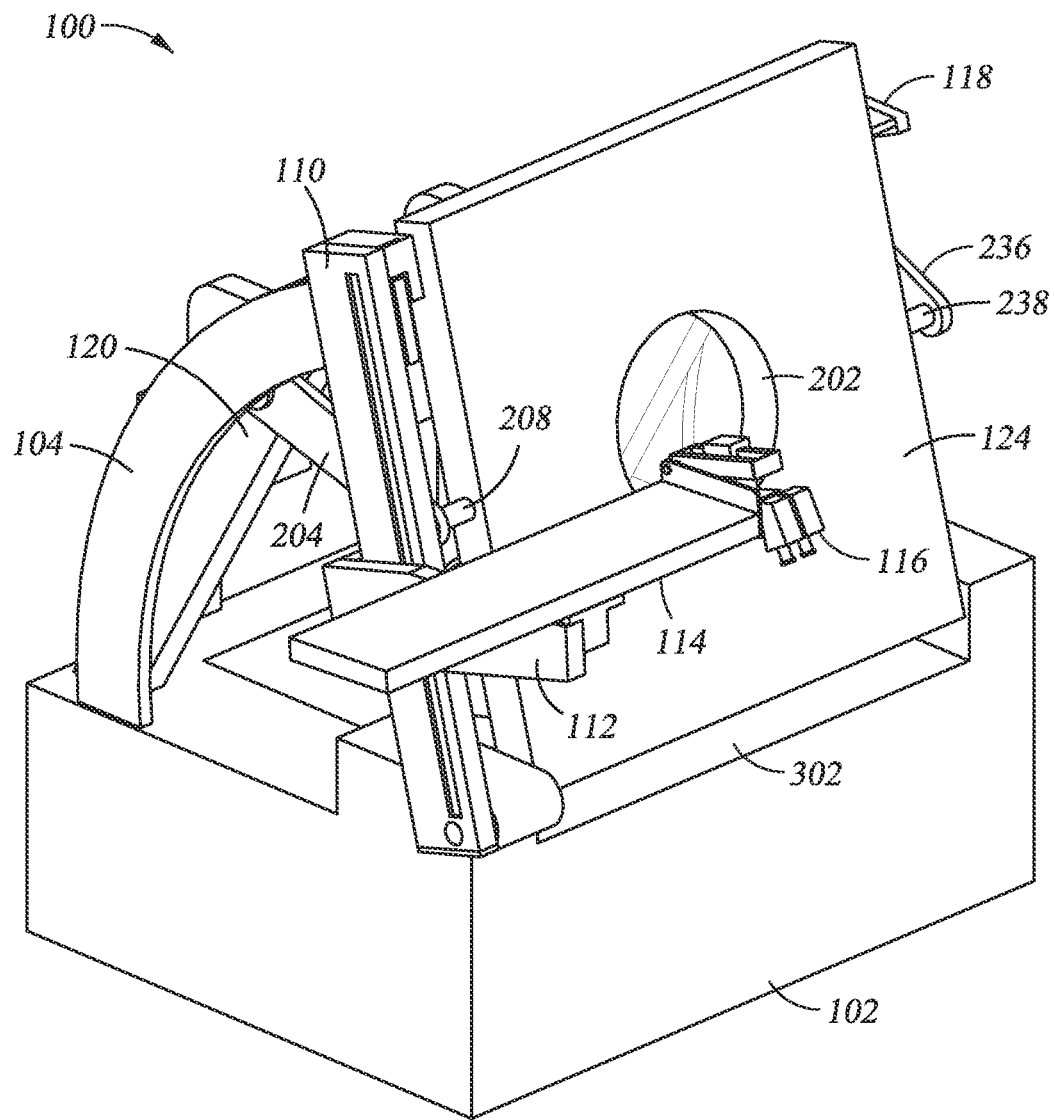
FIG. 3 is a schematic isometric illustration of the probe card analyzer apparatus of FIG. 1 with the analysis table and the sample table in a third position.

As shown in FIG. 3, the sample table 124 rests in a ledge 302 formed in the body 102. The sample table 124 also rests on the beam 118. The microscope 116 is positioned so that the probe cards can be viewed on the sample table 124 while the sample table 124 is in the third position.

Figure 4A:
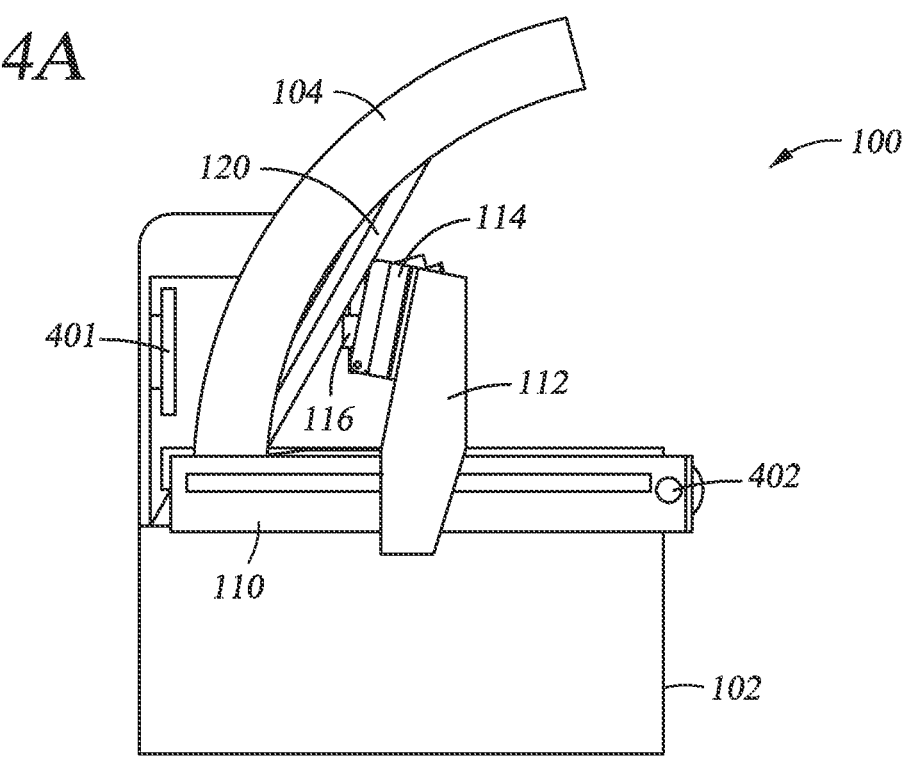
FIGS. 4A-4T are schematic side views of the probe card analyzer apparatus of FIG. 1 at various stages of movement.
Figure 4B:
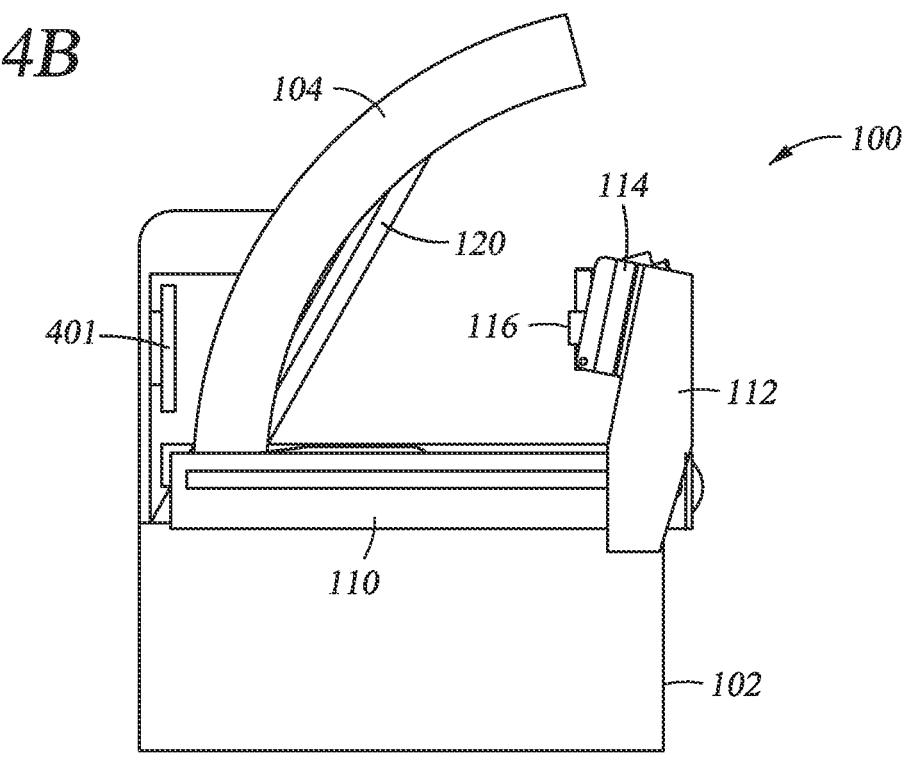
Figure 4C:
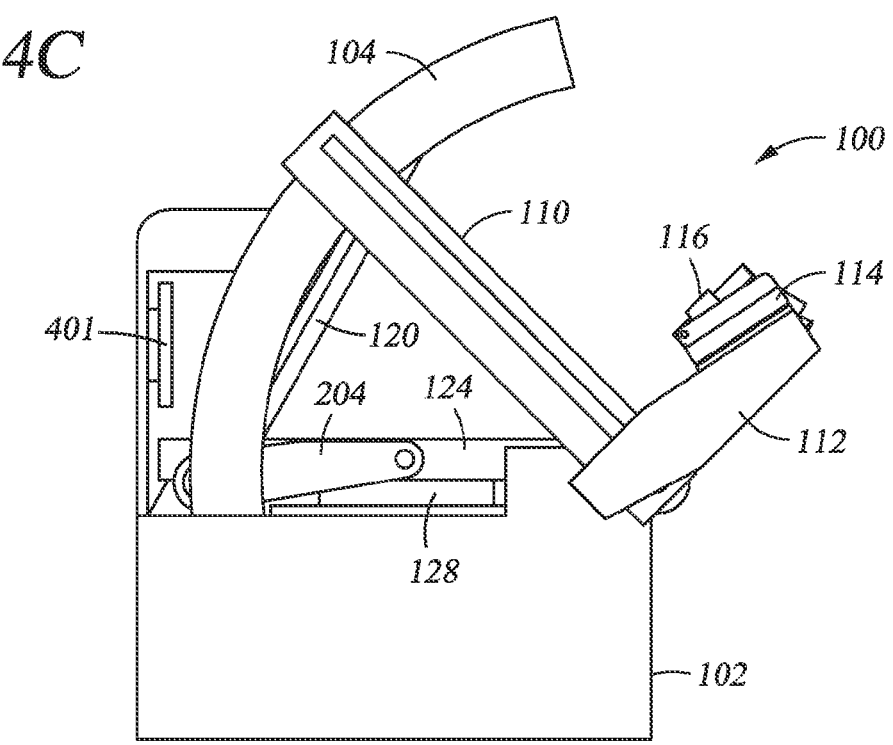
Figure 4D:
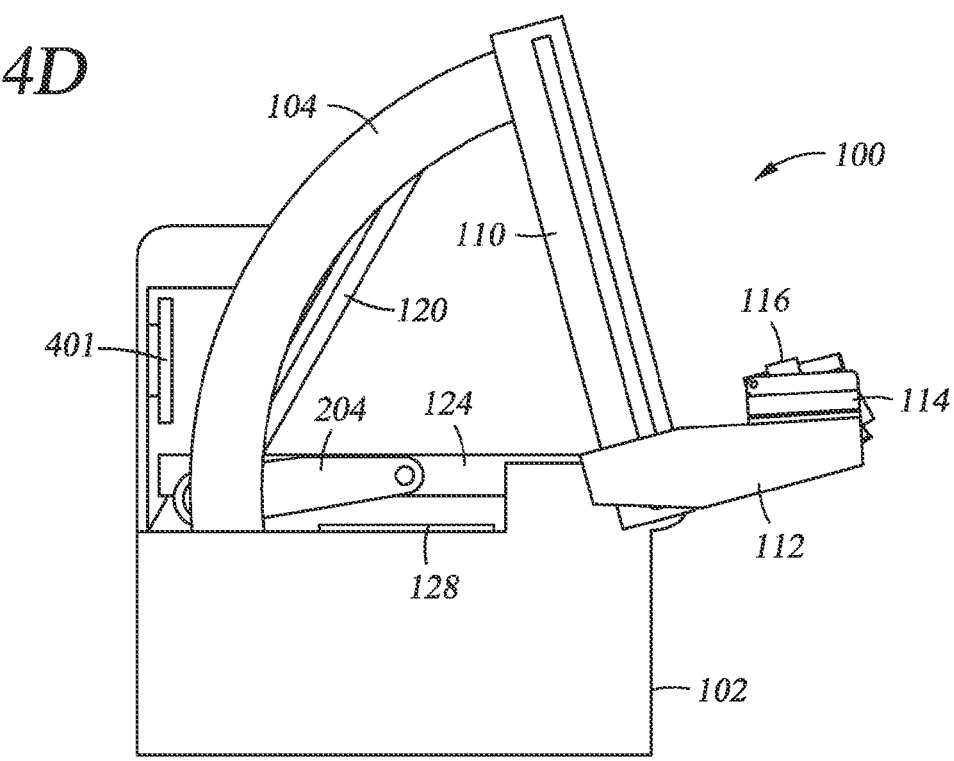
Figure 4E:
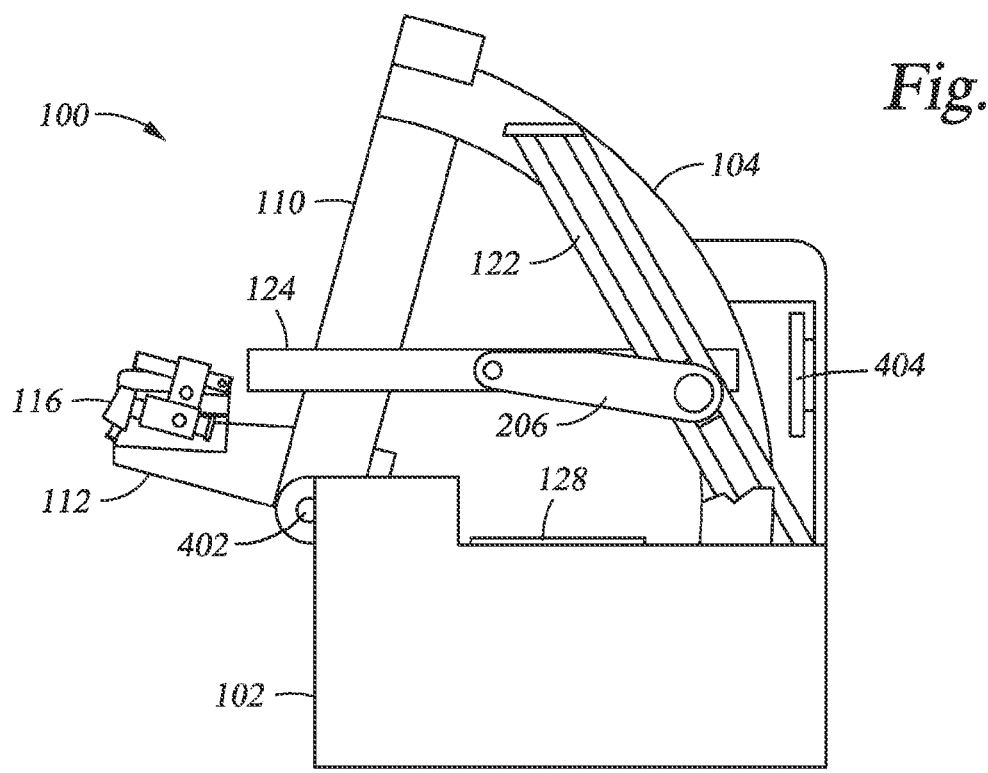
Figure 4F:
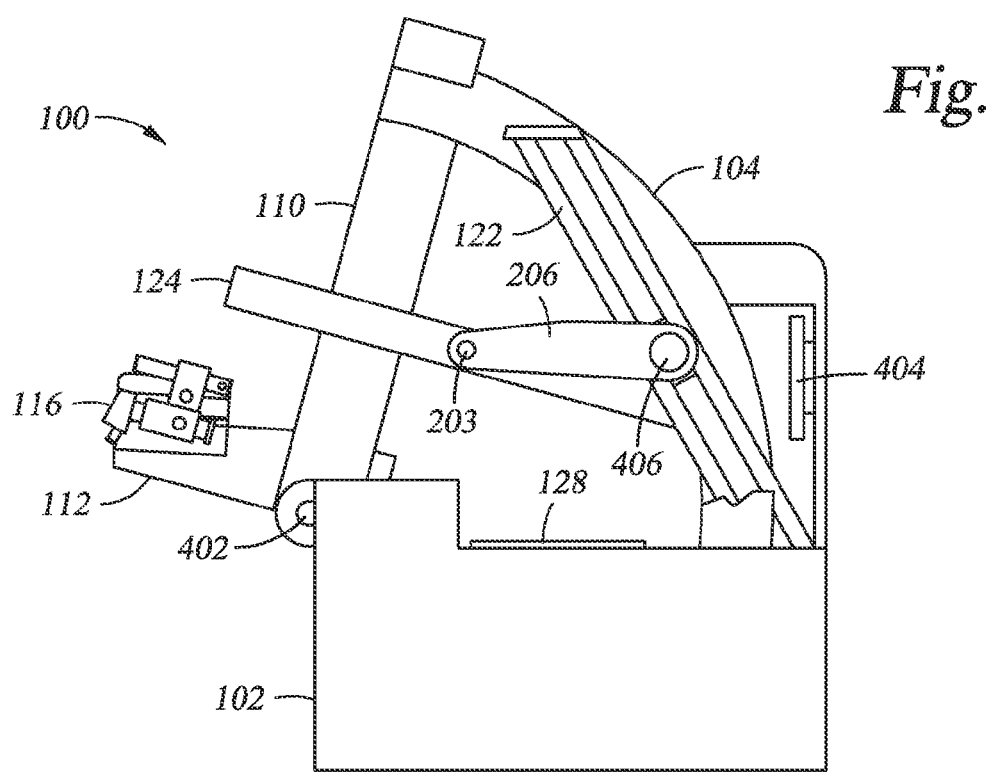
Figure 4G:
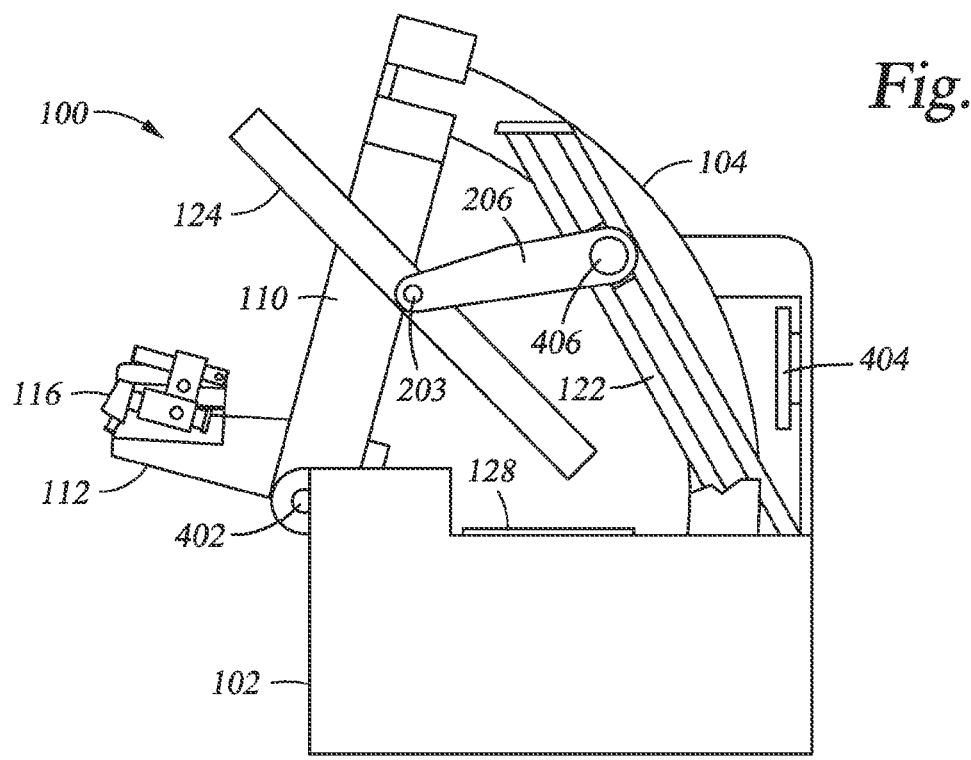
Figure 4H:
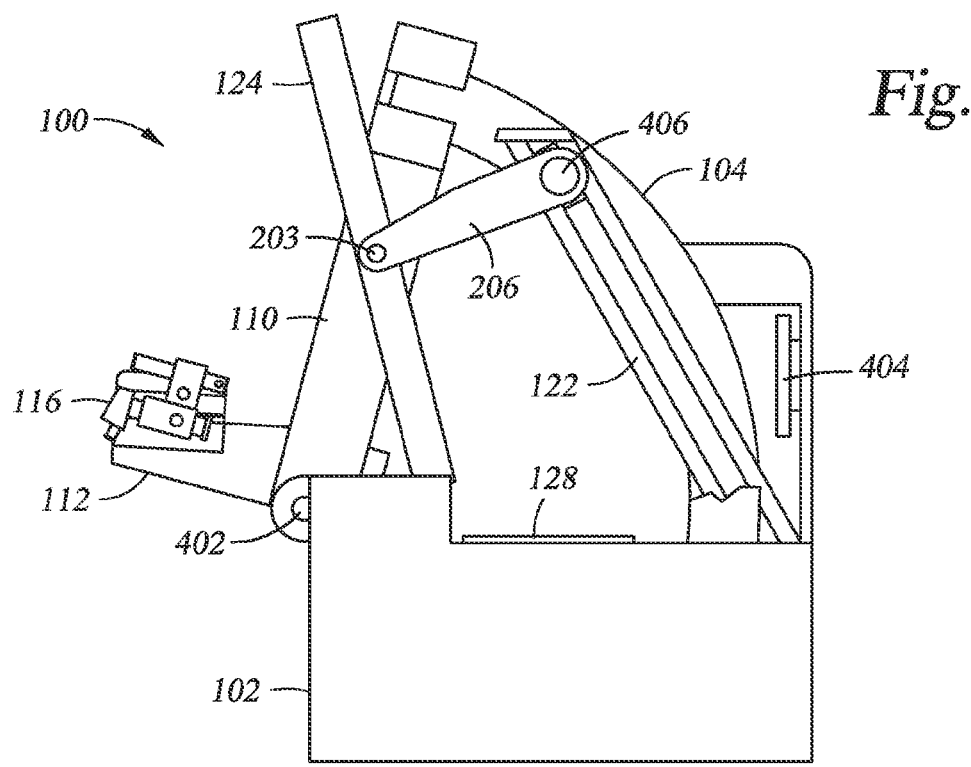
Figure 4I:
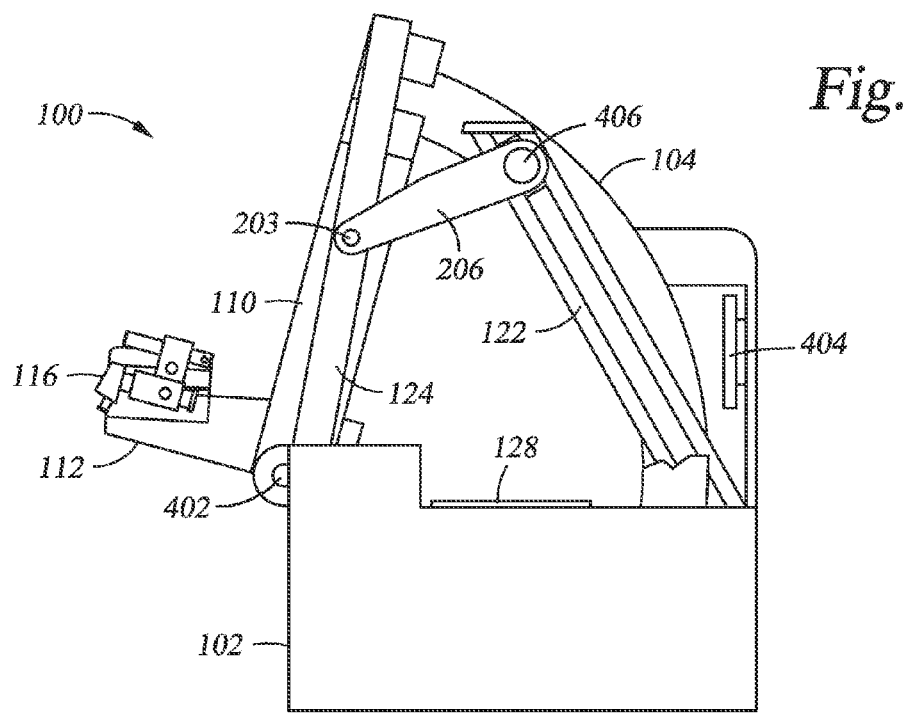
Figure 4J:
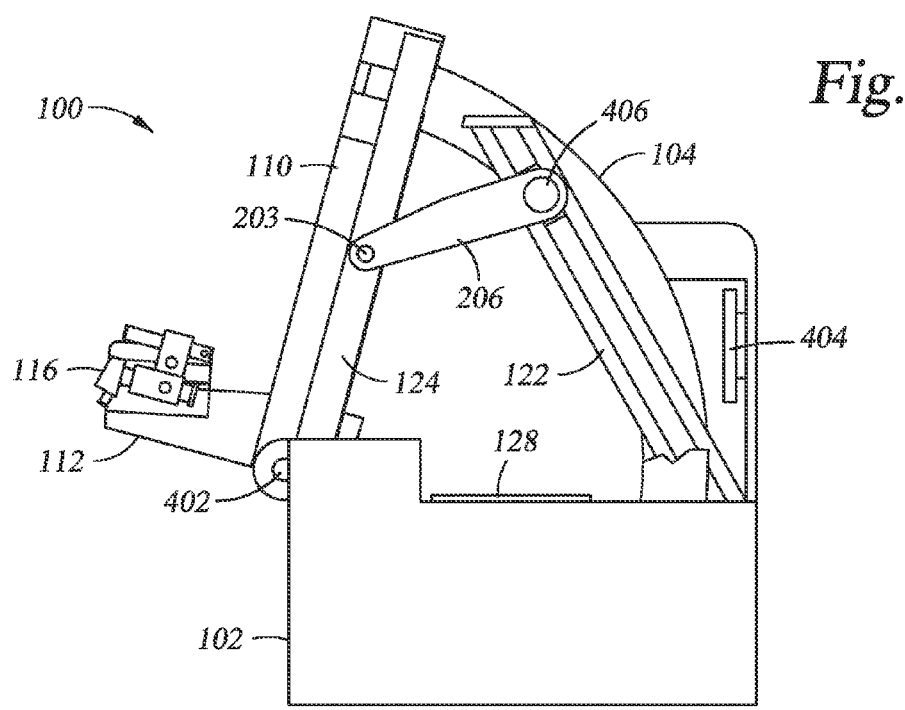
Figure 4K:
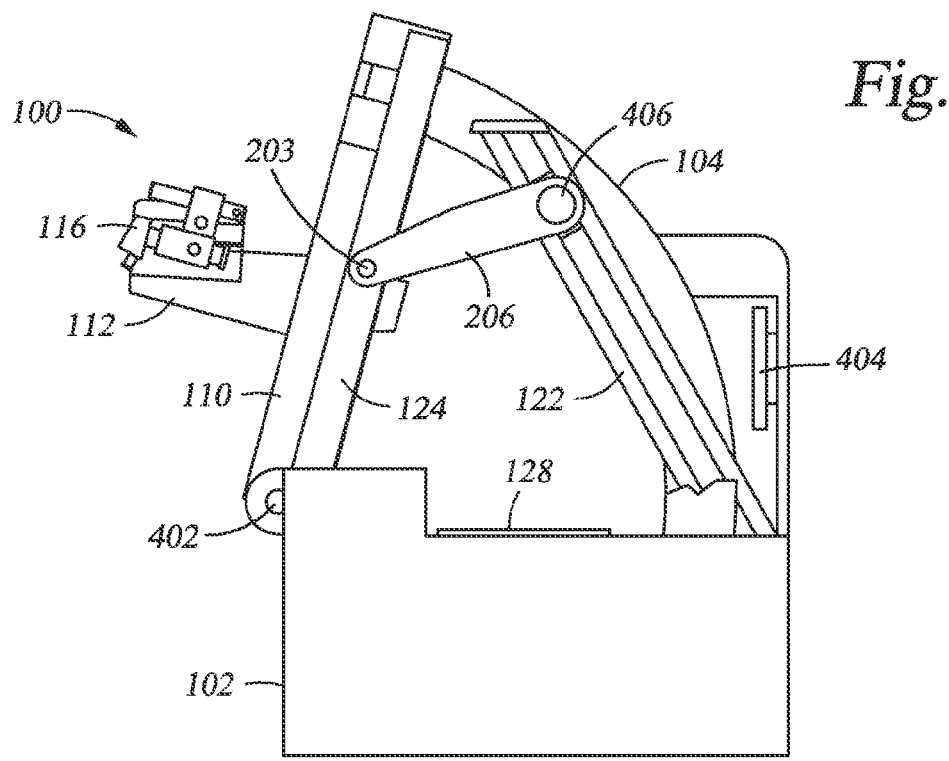
Figure 4L:
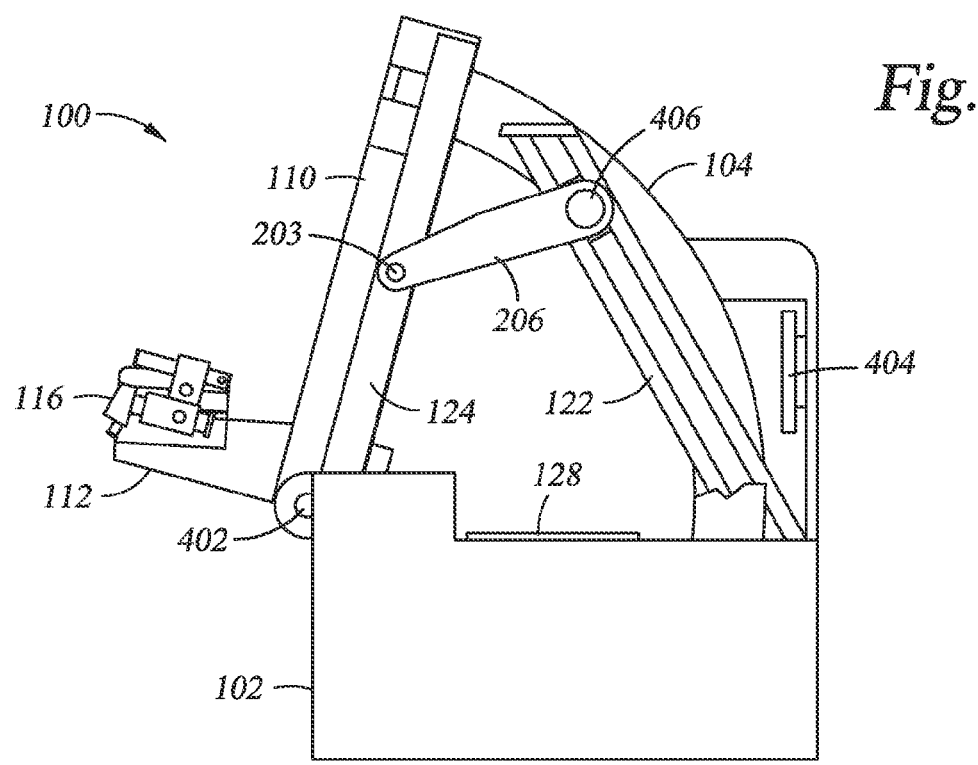
Figure 4M:
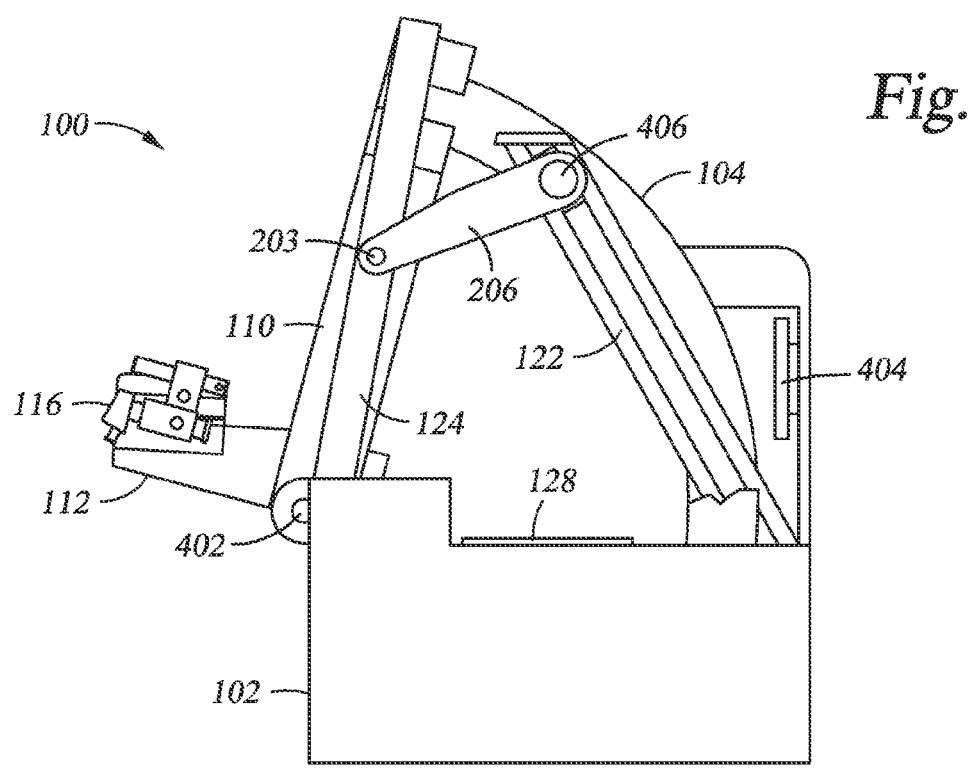
Figure 4N:
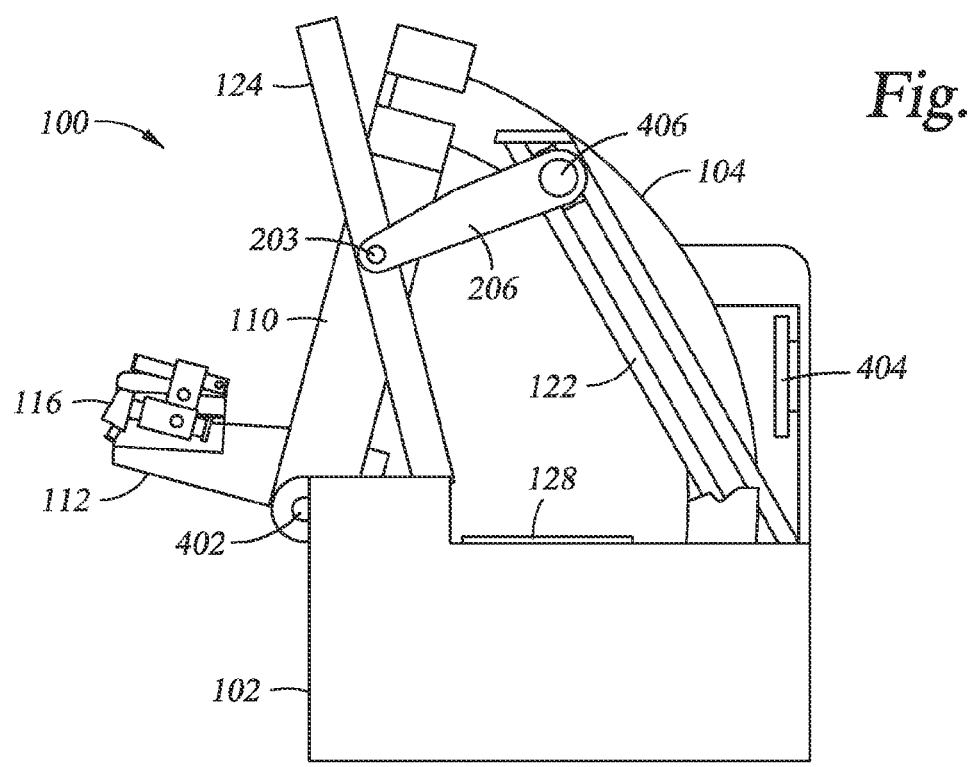
Figure 4O:
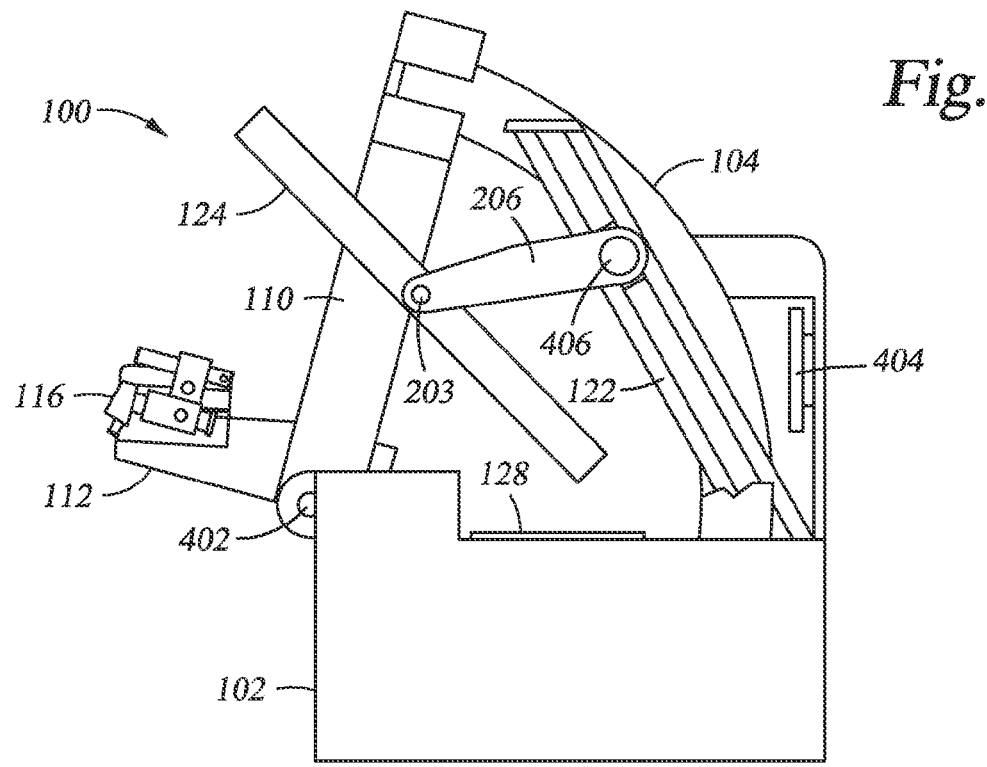
Figure 4P:
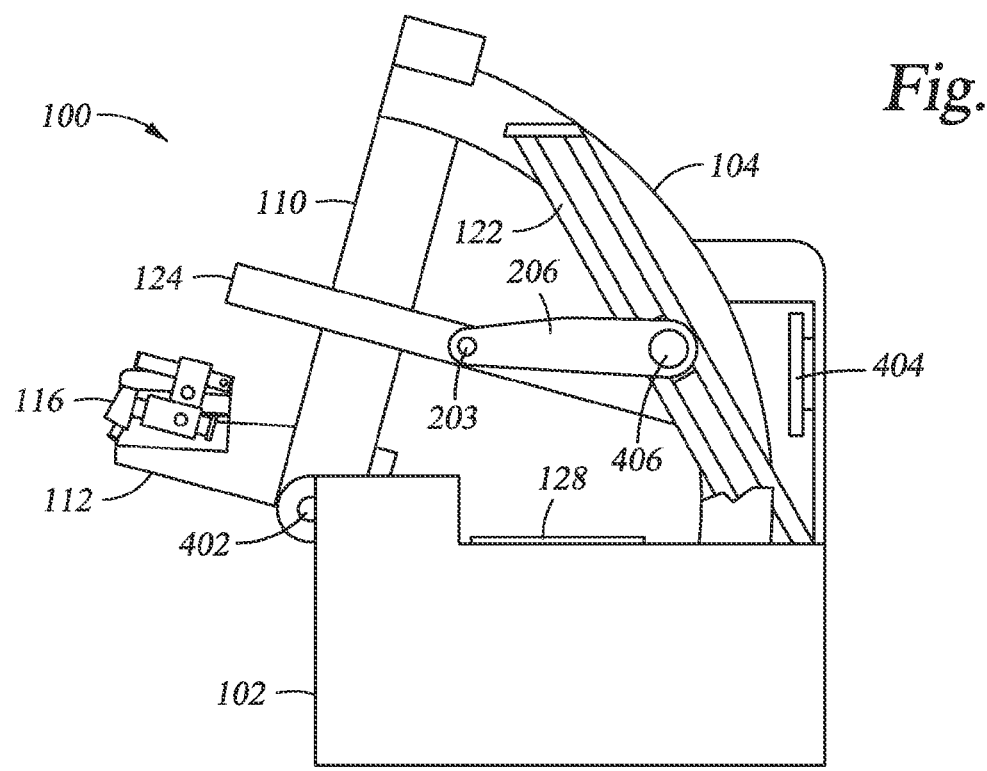
Figure 4Q:
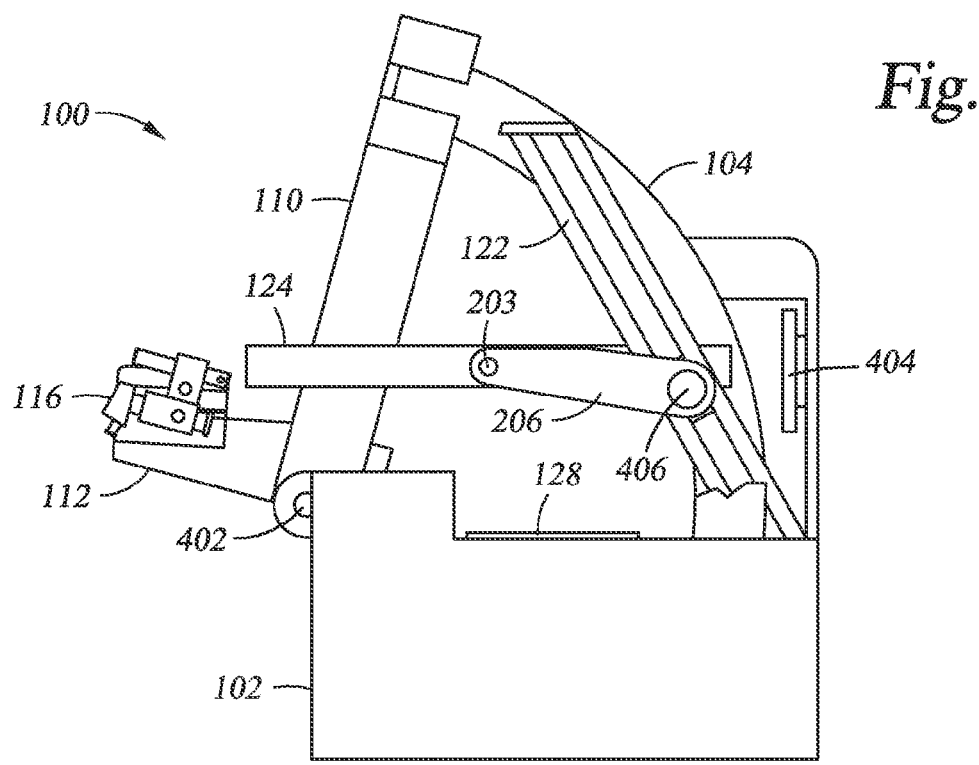
Figure 4R:
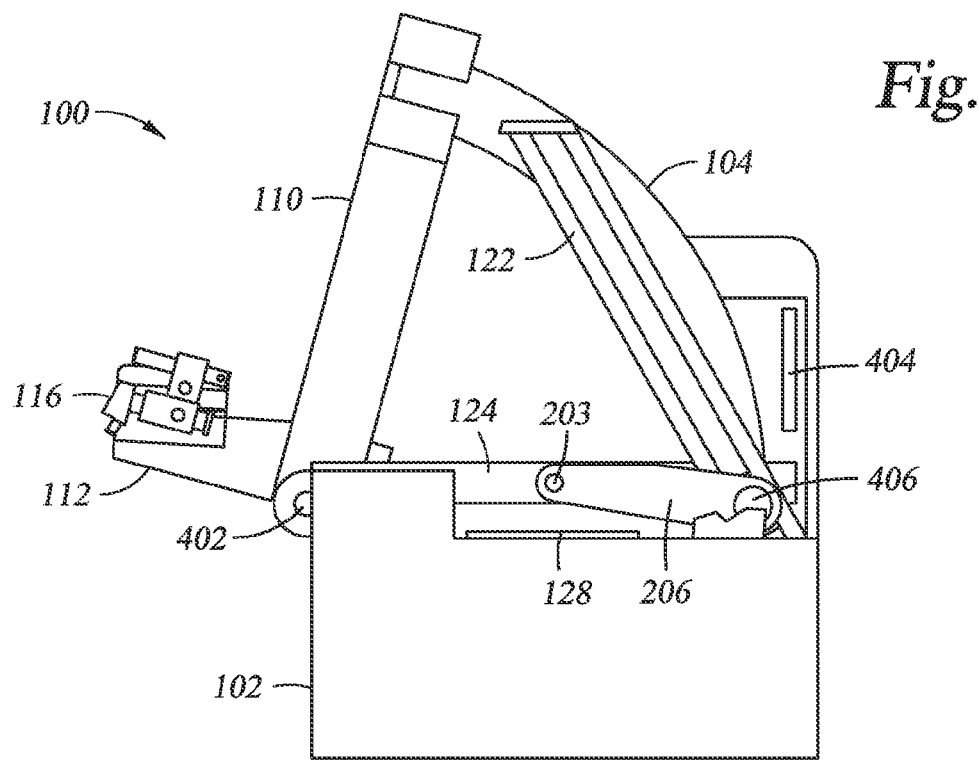
Figure 4S:
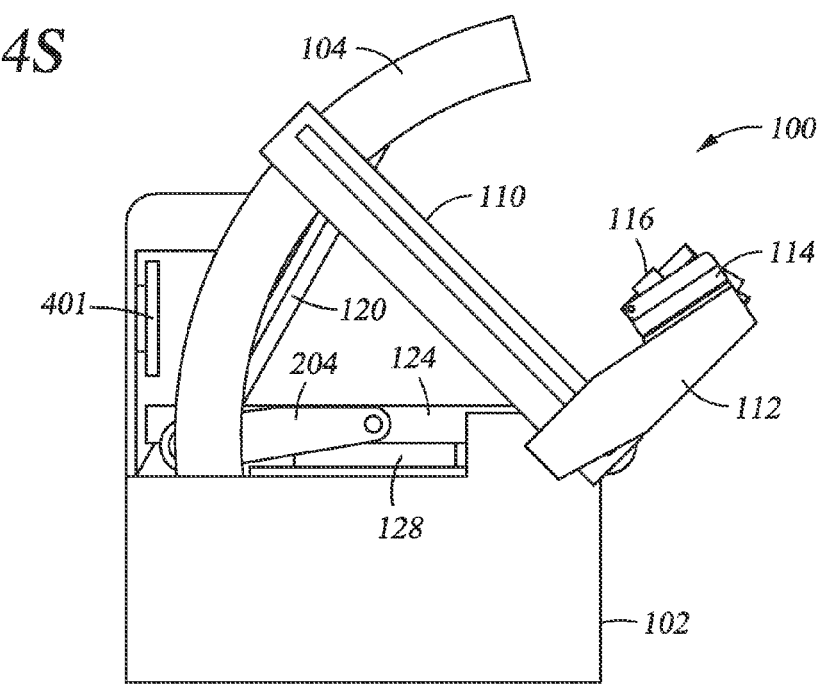
Figure 4T:
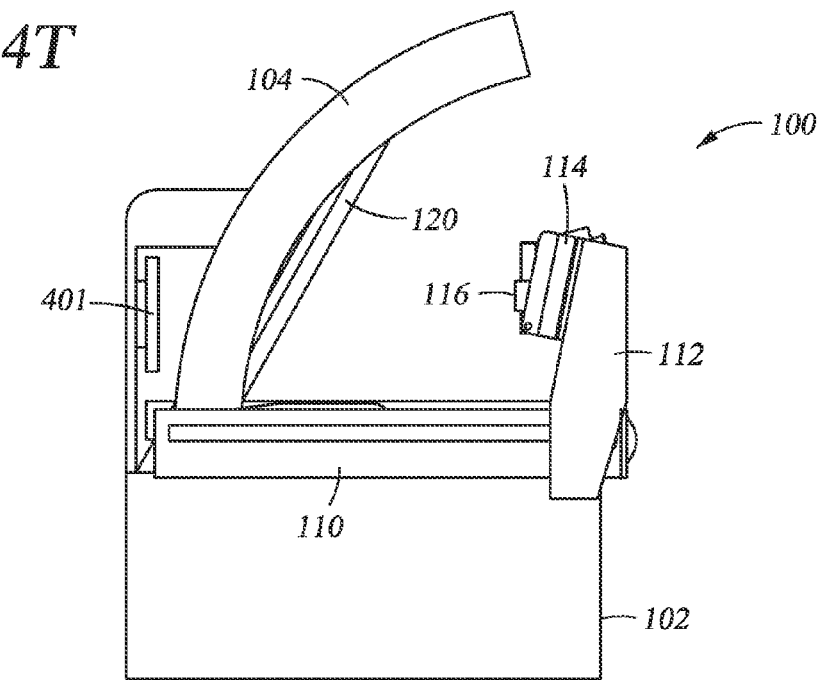

FIGS. 4A-4T are schematic side views of the probe card analyzer apparatus 100 at various stages of movement. Initially, the sample table 124 is substantially flat against the body 102 as shown in FIG. 4A prior to movement. Then, as shown in FIG. 4B, the second analysis arm 112 slides along the first analysis arm 110. As noted above, the first analysis arm 110 can pivot about axis 402. Additionally shown in FIG. 4A is a computer terminal 404 which receives input from the microscope 116.

Once the second analysis arm 112 has fully retracted to the end of the first analysis arm 110 furthest away from the first support arm 104, the first analysis arm 110 then pivots or rotates about axis 402 so that the first analysis arm 110 moves along the first support arm 104 as shown in FIG. 4C. As the first analysis arm 110 slides along the first support arm 104, the first sample table arm 204 becomes visible as does the sample table 124 and the cylinder 128 until the first analysis arm 110 has fully pivoted/rotated and reached the end of the first support arm 104 as shown in FIG. 4D.

FIGS. 4E-4R illustrate the apparatus 100 from the opposite side view of FIGS. 4A-4D, 4S and 4T. The second support arm 106 has been removed for clarity. As shown in FIG. 4E, now that the first analysis arm 110 has fully pivoted/rotated and reached the end of the first support arm 104, the sample table 124 may begin to move. Prior to movement, the cylinder 128 retracts into the body 102. Thereafter, the second sample table arm 206 begins to move along the track 122 and cause the sample table 124 to raise from the body 102. During the movement of the second sample table arm 206, and hence, the fifth arm 204 (not visible), the sample table 124 begins to rotate clockwise about an axis 208 as shown in FIGS. 4F-4H until the sample table extends out above the ledge 302. At this point, the first and second sample table arms 204, 206 have reached the end of the tracks 120, 122 as shown in FIG. 4H.

As shown in FIG. 4I, the second sample table arm 206 then rotates/pivots about an axis 406 simultaneously with the sample table 124 rotating/pivoting about an axis 208 such that the sample table 124 first rests in the ledge 302 as shown in FIG. 4I. The first and second sample table arms 204, 206 then slide back down the respective tracks 120, 122 as shown in FIG. 4J such that the sample table 124 then rests against the beam 118. The second analysis arm 112 then may slide along the first analysis arm 110 as shown in FIG. 4K to position the analysis table 114 and hence, the microscope 116 in position to examine a probe card. It should be noted that the sample table 124, when in the position shown in FIG. 4K to be analyzed by the microscope 116 has the opposite side of the sample table 124 facing the microscope 116 as compared to FIG. 4A due to the rotation of the sample table 124 during movement. Thus, both sides of a probe card can be analyzed on one apparatus.

FIGS. 4L-4T show the movement of the sample table 124 back to the original position. As shown in FIGS. 4L and 4M, after the microscope 116 and second analysis arm 112 have moved out of the way, the first and second sample table arms 204, 206 move along the respective tracks 120, 122 to push the sample table 124 away from the beam 118. Thereafter, the first and second sample table arms 204, 206 rotate/pivot about axis 406 while the sample table 124 rotates about axis 208 to cause the sample table 124 to lift from the ledge 302 as shown in FIGS. 4M and 4N while the first and second sample table arms 204, 206 move along their respective tracks 120, 122 to the end of the tracks. Thereafter, the sample table 124 rotates counterclockwise about axis 208 while the first and second sample table arms 204, 206 move along the respective tracks 120, 122 towards the body 102 as shown in FIGS. 4O-4Q until finally landing in a substantially horizontal position as shown in FIG. 4R. The cylinder 128 may then raise and the first analysis arm 110 may move along the first support arm 104 as shown in FIGS. 4S and 4T while the first analysis arm 110 pivots/rotates about an axis 402.

Figure 5:
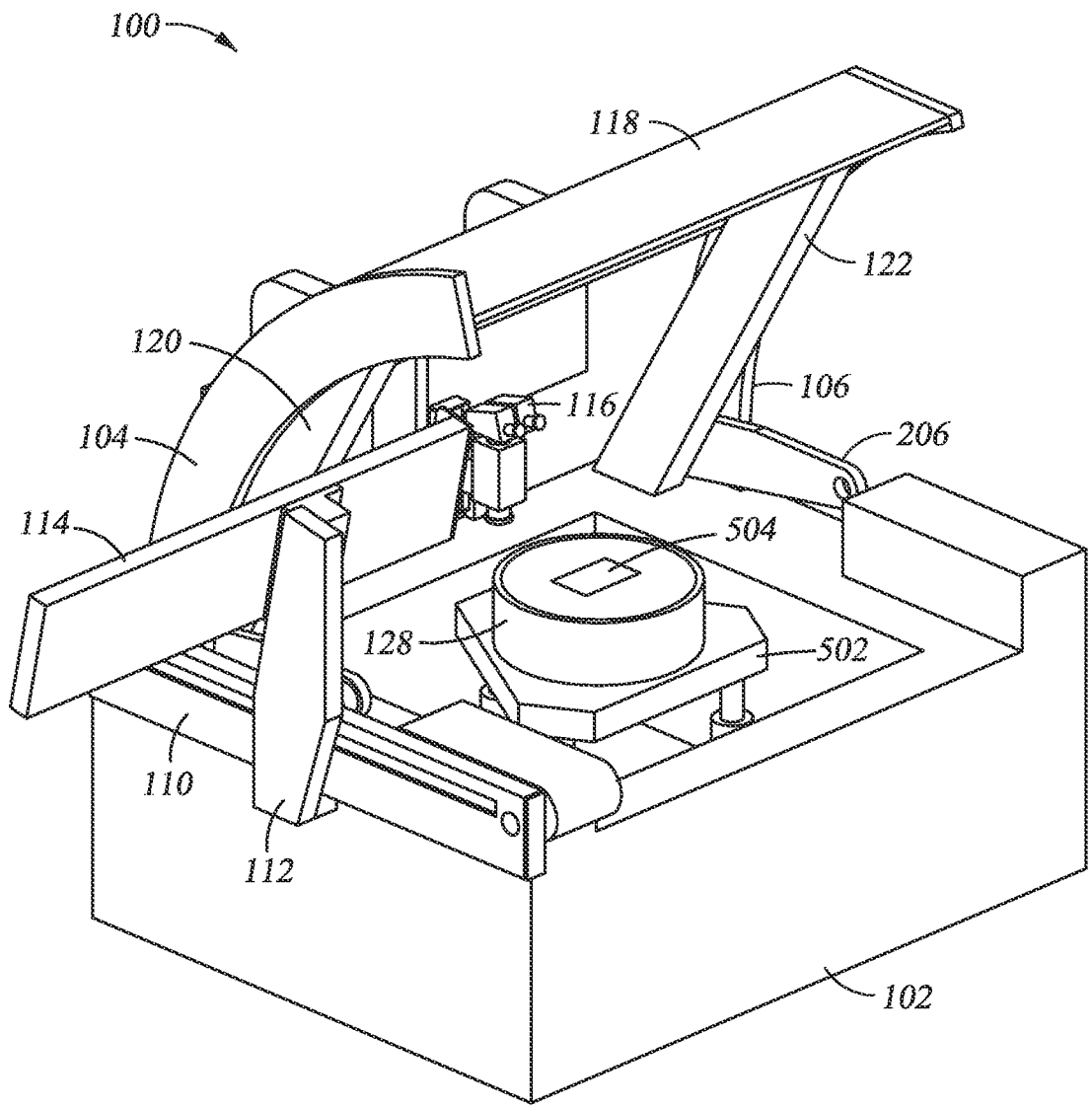
FIG. 5 is a schematic isometric illustration of the probe card analyzer apparatus of FIG. 1 with the sample table removed.

FIG. 5 is a schematic isometric illustration of the probe card analyzer apparatus of FIG. 1 with the sample table removed. As shown in FIG. 5, a camera 504 is present within the cylinder 128 and an alignment mechanism 502 is also present to properly align the cylinder 128 and hence, camera 504. The camera is used to ensure proper alignment of the cylinder 128 and hence, proper analysis of the probe card resting on the cylinder 128 during analysis. The camera 504 operates by looking through an alignment plate (shown in FIG. 7). If the alignment plate is out of alignment, then the cylinder 128 is out of alignment and hence, the alignment mechanism 502 adjusts the cylinder 128.

Figure 6:
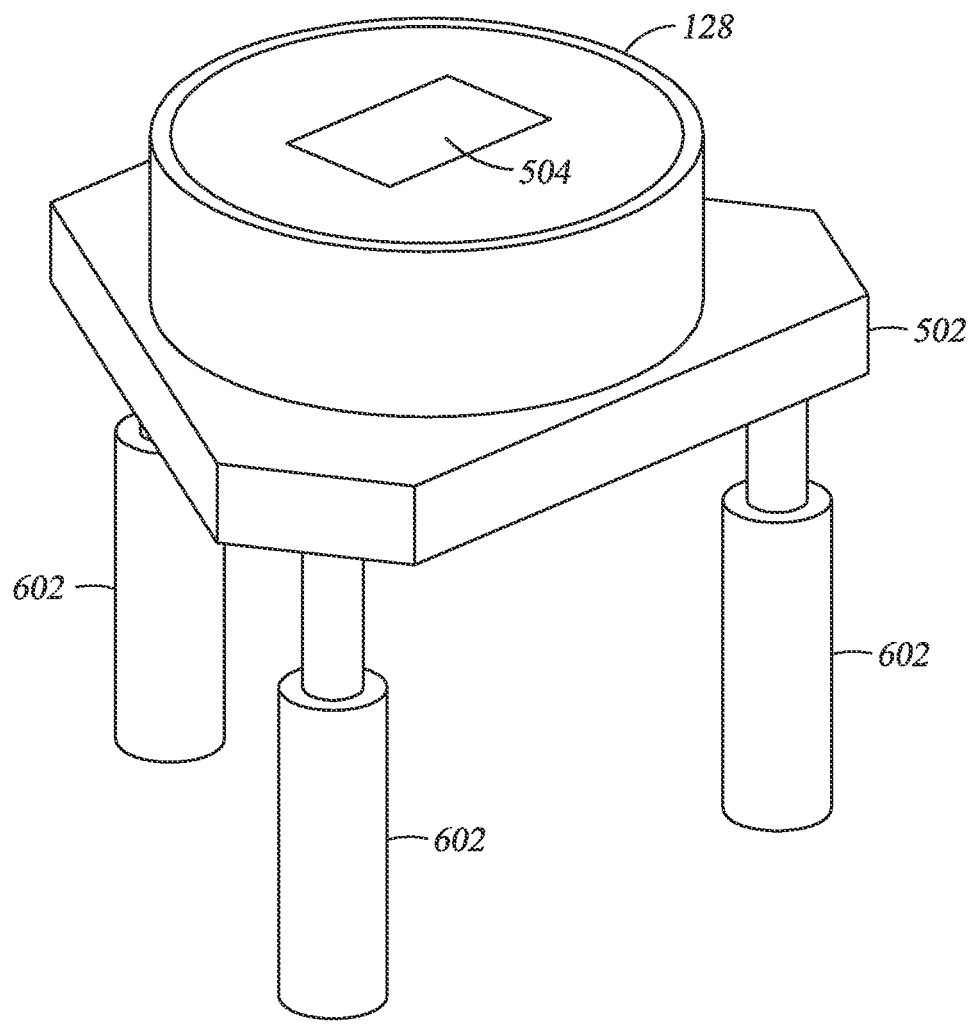
FIG. 6 is a schematic isometric illustration of the cylinder and alignment mechanism according to one embodiment.

FIG. 6 is a schematic isometric illustration of the cylinder 128 with alignment mechanism 502 according to one embodiment. Whenever the cylinder is out of alignment, the three corners of the alignment mechanism 502 are adjusted as needed with alignment devices 602 that raise or lower the corner of the alignment mechanism 502. The three alignment devices 602 are operated by three separate z-stages to move and level the alignment mechanism 502 and hence, the probe card resting on the cylinder 128.

Figure 7:
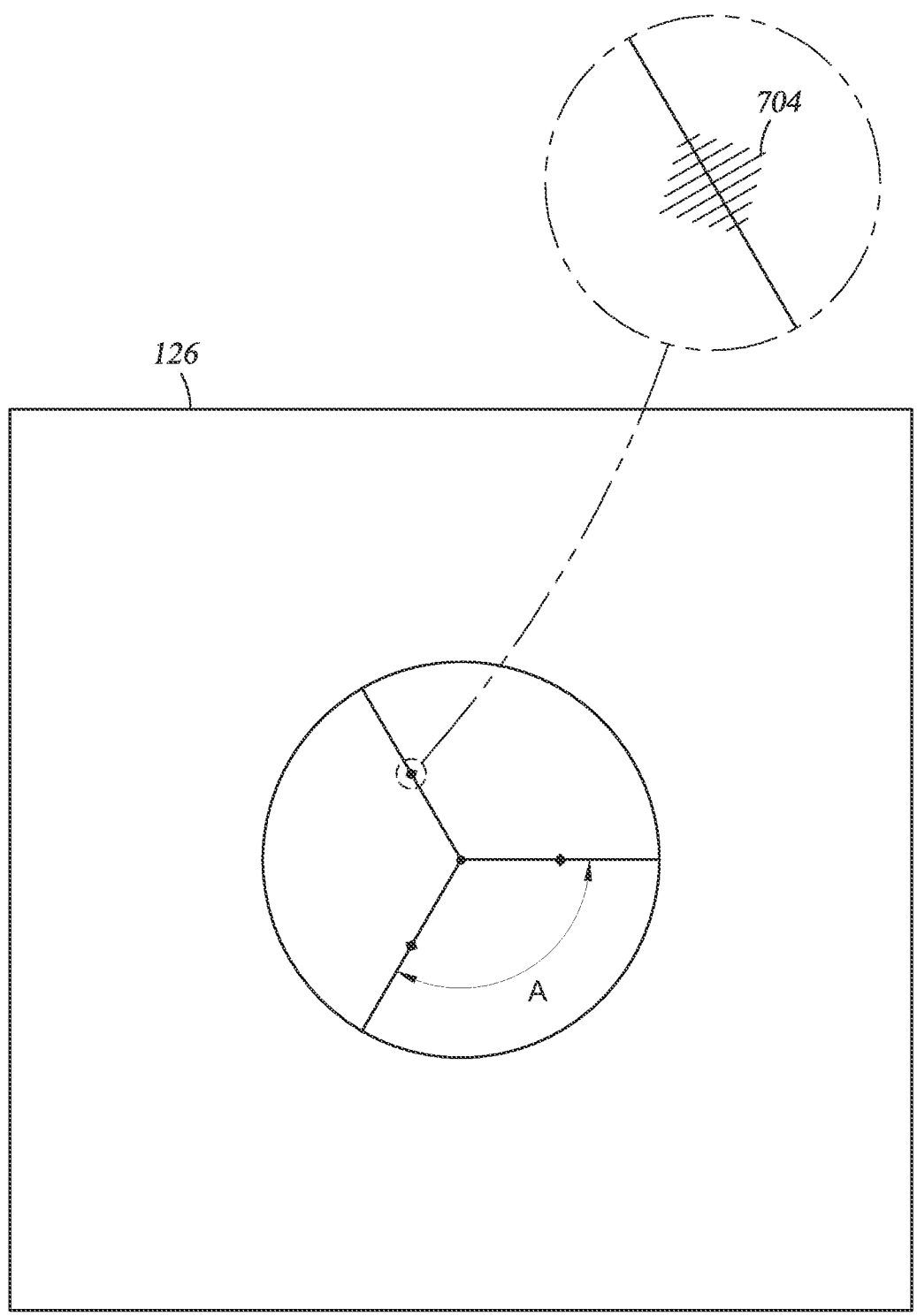
FIG. 7 is a schematic illustration of an alignment plate according to one embodiment.

FIG. 7 is a schematic illustration of an alignment plate 126 according to one embodiment. As shown in FIG. 7, the alignment plate 126 includes three alignment marks 704 that are located along radius that are 120 degrees apart as shown by arrow "A". It is to be understood that more alignment marks may be used if desired. The alignment marks 704 include a plurality of lines. When the lines are in focus for all alignment marks 704 when viewed from the camera 504, the cylinder 128 is properly aligned and hence, the probe card is properly aligned for analysis. The alignment marks 704 may comprise copper.

The camera 504 operates as a fast scanning camera and scans the probes of the probe card. The camera scans a linear path under the alignment plate 126 taking pictures of the probes of the probe card to find all of the probes. The computer 404 analyzes the results by comparing the images from the camera 504 to expected results. The alignment plate 126 is lifted up and moved in an x-y direction to align the probe card on the cylinder. Additionally, the computer 404 analyzes the results and the alignment devices 602 move the alignment mechanism 502 in the z direction to properly align the probe card. Additionally, the results of the bad probes are communicated to the technician and the sample table can be rotated for the technician to access the bad probes.

Figure 8:
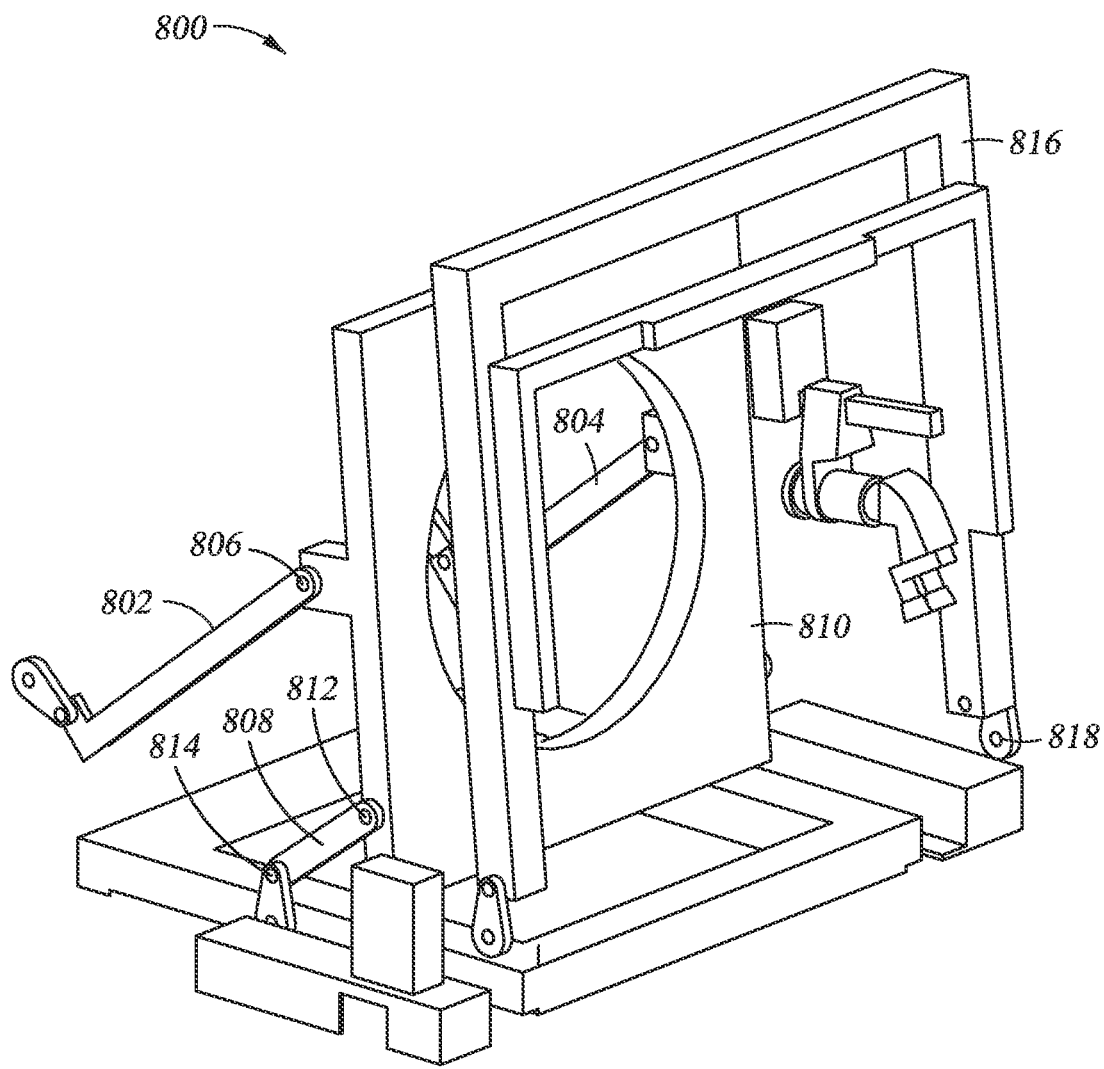
FIG. 8 is a schematic isometric illustration of a probe card analyzer according to another embodiment.

FIG. 8 is a schematic isometric view of a probe card analyzer apparatus 800 according to another embodiment. The apparatus body 102 and tracks 120, 122 have not been shown for clarity. As shown in FIG. 8, the sample table 124 is coupled to first and second sample table arms 802, 804 that are to be coupled to the first and second tracks 120, 122 such that the first and second table arms 802, 802 do not rotate relative to the first and second tracks 120, 122 while moving along the tracks 120, 122. The first and second table arms 802, 804 are rotationally coupled to the sample table 124 such that the sample table 124 can rotate about axis 806 when the first and second arms 802, 804 move along the tracks 120, 122. Third and fourth sample table arms 808, 810 are also coupled to the sample table 124. The third and fourth sample table arms 808, 810 are rotationally coupled to the sample table 124 such that the sample table rotates about axis 812. The third and fourth sample table arms 808, 810 are to be also coupled to the body 102. The third and fourth sample table arms 808, 810 are rotationally coupled to the body 102 such that the third and fourth sample table arms 808, 810 rotate about axis 814. During movement, the third and fourth sample table arms 808, 810 rotate about axis 812, 814 in opposite directions. Additionally, rather than an analysis table 114, the microscope is coupled to a frame assembly 816 that is to be coupled to the third and fourth corners of the body 102 and the frame assembly 816 is rotatable about an axis 818.

By rotating the sample table, the technician can access both the front and the back of the probe cards that are being tested with relative ease.

While the foregoing is directed to embodiments of the present invention, other and further embodiments of the invention may be devised without departing from the basic scope thereof, and the scope thereof is determined by the claims that follow.

The invention claimed is:

1. A probe card analyzer apparatus, comprising:
a table body;
a first support arm extending away from a first corner of the table body;
a second support arm extending away from a second corner of the table body, the second support arm extending substantially parallel to the first support arm;
a first track coupled to the first support arm;
a second track coupled to the second support arm;
a first sample table arm coupled to the first track and movable along the first track;
a second sample table arm coupled to the second track and movable along the second track, the second sample table arm substantially parallel to the first sample table arm;
a sample table rotatably coupled to the first sample table arm and the second sample table arm such that the sample table is rotatable about an axis.

2. The apparatus of claim 1, further comprising a first analysis arm coupled to a third corner of the table body, the first analysis arm pivotable about an axis at the third corner and movable along the first support arm.

3. The apparatus of claim 2, further comprising:
a second analysis arm coupled to the first analysis arm and extending substantially perpendicular to the first analysis arm;
an analysis table coupled to the second analysis arm and movable along the second analysis arm; and
a microscope coupled to the analysis table.

4. The apparatus of claim 3, wherein the microscope further comprises a repair robot comprising a laser mounted on the microscope for cutting a defective probe needle and welding on a new probe needle.

5. The apparatus of claim 4, wherein the sample table is sized to process a probe card having a diameter of about 450 mm.

6. The apparatus of claim 5, wherein the sample table has an opening therethrough.

7. The apparatus of claim 6, further comprising an alignment plate disposed over the opening, wherein the alignment plate comprises at least one optical alignment dot.

8. The apparatus of claim 7, further comprising a camera, wherein the camera is a fast scanning camera wherein the camera moves continuously to allow rapid identification of the at least one optical dot.

9. The apparatus of claim 7, wherein the at least one optical dot is about 120° from a second optical dot relative to the center of the plate.

10. The apparatus of claim 7, wherein the at least one optical dot comprises copper or glass.

11. The apparatus of claim 7, further comprising at least one Z stage for leveling a probe card to a parallel position with the sample table.

12. The apparatus of claim 1, wherein the sample table has an opening therethrough.

13. The apparatus of claim 12, further comprising an alignment plate disposed over the opening, wherein the alignment plate comprises at least one optical alignment dot.

14. The apparatus of claim 13, further comprising a camera, wherein the camera is a fast scanning camera wherein the camera moves continuously to allow rapid identification of the at least one optical dot.

15. The apparatus of claim 13, wherein the at least one optical dot is about 120° from a second optical dot relative to the center of the plate.

16. The apparatus of claim 13, wherein the at least one optical dot comprises copper.

17. The apparatus of claim 13, further comprising at least one Z stage for leveling a probe card to a parallel position with the flip table.

18. The apparatus of claim 1, further comprising at least one Z stage for leveling a probe card to a parallel position with the flip table.

19. A method for moving a sample table in a probe tester apparatus, comprising:
    moving a first sample table arm along a first track that is coupled to a first support arm that is coupled to a first corner of a table body;
    moving a second sample table arm along a second track that is coupled to a second support arm that is coupled to a second corner of the table body, wherein the second support arm is in a plane substantially parallel to a plane in which the first support arm is disposed; and
    rotating a sample table about an axis, wherein the sample table is rotatably coupled to the first sample arm and the second sample arm.

20. The method of claim 19, further comprising pivoting a first analysis arm about an axis and moving the first analysis arm along the first support arm, wherein the first analysis arm is coupled to a third corner of the table body.

21. A probe card analyzer apparatus, comprising:
    a table body;
    a first support arm extending away from a first corner of the table body;
    a second support arm extending away from a second corner of the table body, the second support arm extending substantially parallel to the first support arm;
    a first track coupled to the first support arm;
    a second track coupled to the second support arm;
    a first sample table arm coupled to the first track and movable along the first track;
    a second sample table arm coupled to the second track and movable along the second track, the second sample table arm is substantially parallel to the first sample table arm;
    a third sample table arm pivotably coupled to the table body;
    a fourth sample table arm pivotably coupled to the table body; and
    a sample table rotatably coupled to the first sample table arm, the second sample table arm, the third sample table arm and the fourth sample table arm such that the sample table is rotatable about one or more axis.

* * * * *